US008657775B2

(12) United States Patent
Hutchison et al.

(10) Patent No.: US 8,657,775 B2
(45) Date of Patent: Feb. 25, 2014

(54) METHOD OF TREATING A SUBJECT SUFFERING FROM END STAGE RENAL DISEASE AGAINST CARDIOVASCULAR DISEASE

(75) Inventors: Colin Hutchison, Birmingham (GB); Paul Cockwell, Birmingham (GB); Hermann Göhl, Bisingen (DE); Bernd Krause, Rangendingen (DE); Markus Storr, Filderstadt (DE)

(73) Assignee: Gambro Lundis AB, Lund (SE)

( * ) Notice: Subject to any disclaimer, the term of this patent is extended or adjusted under 35 U.S.C. 154(b) by 368 days.

(21) Appl. No.: 12/585,054

(22) Filed: Sep. 1, 2009

(65) Prior Publication Data

US 2010/0084339 A1    Apr. 8, 2010

(30) Foreign Application Priority Data

Sep. 3, 2008 (EP) .................................. 08015529

(51) Int. Cl.
*A61M 1/14* (2006.01)
*A61M 1/18* (2006.01)
*A61M 1/34* (2006.01)
*B01D 61/24* (2006.01)
*B01D 61/28* (2006.01)
*B01D 69/08* (2006.01)
*B01D 63/02* (2006.01)

(52) U.S. Cl.
USPC ............ 604/5.04; 210/321.6; 210/321.78; 210/321.79; 210/321.8; 210/321.87; 210/321.88; 210/321.89; 210/500.21; 210/500.23; 210/645; 210/646; 210/649; 604/4.01; 604/5.01; 604/6.09

(58) Field of Classification Search
USPC ............ 210/645, 646, 649, 321.6, 321.78, 210/321.79, 321.8, 321.87, 321.88, 321.89, 210/500.21, 500.23; 604/4.01, 5.01, 5.04, 604/6.09
See application file for complete search history.

(56) References Cited

U.S. PATENT DOCUMENTS

2006/0144782 A1*   7/2006   Buck ........................ 210/500.23
2007/0251882 A1*  11/2007   Bradwell et al. .............. 210/646

FOREIGN PATENT DOCUMENTS

EP          0 305 787 A       3/1989
EP          1 852 136 A      11/2007
WO       WO 2004/056460       7/2004

OTHER PUBLICATIONS

Morgera, S. et al., "Renal Replacement Therapy With High-Cutoff Hemofilters: Impact of Convection and Diffusion on Cytokine Clearances and Protein Status", American Journal of Kidney Diseases, vol. 43, No. 3, Mar. 2004: pp. 444-453.

Foley, R. et al., "Clinical Epidemiology of Cardiovascular Disease in Chronic Renal Disease", American Journal of Kidney Diseases, vol. 32, No. 5, Suppl 3, Nov. 1998: pp. S112-S119.

(Continued)

*Primary Examiner* — John Kim
(74) *Attorney, Agent, or Firm* — Barnes & Thornburg LLP

(57) ABSTRACT

The present invention relates to high cut-off hemodialysis membranes for the treatment of chronic hemodialysis (CHD) patients, with the potential to improve long-term survival of these patients by reducing the risk of cardiovascular disease, through down-regulation of monocyte activation in the blood. Monocytes are the major circulating blood cells involved in the progression of cardiovascular disease. High cut-off hemodialysis in chronic dialysis patients results in a sustained decrease in expression of monocyte cell-surface proteins that direct the movement of these cells from the blood to the walls of blood vessels, where they promote the progression of arterial disease (atherosclerosis) that leads to cardiovascular disease (CVD); heart disease, strokes and peripheral vascular disease.

8 Claims, 17 Drawing Sheets

(56) References Cited

OTHER PUBLICATIONS

Ziegler-Heitbrock, L., The CD14+ CD16+ blood monocytes: their role in infection and inflammation, Journal of Leukocyte Biology, vol. 81, Mar. 2007, pp. 584-592.

Barlic, J. and Murphy, P., "Chemokine regulation of atherosclerosis", Journal of Leukocyte Biology, vol. 82, Aug. 2007, pp. 226-236.

Ward, R., "Protein-Leaking Membranes for Hemodialysis: A New Class of Membranes in Search of an Application?", Journal of the American Society of Nephrology 16:2421-2430, 2005.

Morgera, S. et al., "High permeability haemofiltration improves peripheral blood mononuclear cell proliferation in septic patients with acute renal failure", Nephrology Dialysis Transplantation, vol. 18, 2003: pp. 2570-2576.

Morgera, S. et al., "Intermittent high permeability hemofiltration in septic patients with acute renal failure", Intensive Care Medicine, 2003, vol. 29, No. 11, pp. 1989-1995.

Cinel, Ismail and Steven M. Opal, "Molecular biology of inflammation and sepsis: A primer," Crit. Care Med. vol. 37, No. 1, 291-304 (2009).

Locatelli, Francesco, Bernard Canaud, Kai-Uwe Eckardt, Peter Stenvinkel, Christoph Wanner and Carmine Zoccali, "Oxidative stress in end-stage renal disease: an emerging threat to patient outcome," Nephrol Dial Transplant, vol. 18, pp. 1272-1280 (2003).

Witko-Sarsat, Véronique, Miriam Friedlander, Thao Nguyen Khoa, Chantal Capeillère-Blandin, Anh Thu Nguyen, Sandrine Canteloup, Jean-Michel Dayer, Paul Jungers, Tilman Drüeke and Béatrice Descamps-Latscha, "Advanced Oxidation Protein Products as Novel Mediators of Inflammation and Monocyte Activation in Chronic Renal Failure," J Immunol, vol. 161, pp. 2524-2532 (1998).

"Latest news from Gambro research relating to hyperinflammation: 360° vitality," 14 pages, 2009.

Razhegi, Effat, Homeira Omati, Sima Maziar, Patricia Khashayar and Mitra Mahdavi-Mazdeh, "Chronic Inflammation Increases Risk in Hemodialysis Patients," Saudi J Kidney Dis Transplant, vol. 19, No. 5, pp. 785-789 (2008).

* cited by examiner

METHOD OF TREATING A SUBJECT SUFFERING FROM END STAGE RENAL DISEASE AGAINST CARDIOVASCULAR DISEASE

FIELD OF THE INVENTION

The present invention relates to high cut-off hemodialysis membranes for the treatment of chronic hemodialysis (CHD) patients, with the potential to improve long-term survival of these patients by reducing the risk of cardiovascular disease, through down-regulation of monocyte activation in the blood. Monocytes are the major circulating blood cells involved in the progression of cardiovascular disease. High cut-off hemodialysis in chronic dialysis patients results in a sustained decrease in expression of monocyte cell-surface proteins that direct the movement of these cells from the blood to the walls of blood vessels, where they promote the progression of arterial disease (atherosclerosis) that leads to cardiovascular disease (CVD); heart disease, strokes and peripheral vascular disease.

BACKGROUND OF THE INVENTION

Cardiovascular disease is the largest single cause of mortality in the general population. The incidence of CVD is far higher in patients with renal disease; the relative risk of CVD directly relates to age and the severity of renal disease. In chronic dialysis patients aged 45 years or younger, cardiac mortality is more than 100-fold greater than in the general population, and whilst this relative risk falls with age, it is still at least fivefold higher in elderly end-stage renal disease (ESRD) patients than in age matched general population (Foley, R., et al., *Am. J. Kidney Dis.* 32, 1998, S112-S119).

Monocytes play a crucial role in the development of atherosclerosis. They originate from the myeloid line of differentiating cells in the bone marrow. Blood monocytes are heterogeneous and may exist in a number of different phenotypic states. The main monocyte population in humans is CD14; CD62L+CCR2+ and is characterized by recruitment to inflammatory sites (NRI review) (see, for review, Ziegler-Heitbrock, L., *J. Leucoc. Biol.* 81, 2007, 584-592). The migration of monocytes is dependent on cognate interactions with endothelial cells. These interactions represent a multi-step process that depends on the expression of a number of molecules on the surface of circulating mononuclear cells.

The initial stages of monocyte recruitment to extravascular sites depends on the rolling of monocytes on endothelial cells. This process is facilitated by binding of (endothelial) cell surface proteins called selectins with glycoprotein ligands on the surface of circulating cells. One of the most important interactions in this group is between monocyte expressed p-selectin glycoprotein ligand-1 (PSGL-1/CD162) and endothelium expressed e-selectin and p-selectin; a recent study in an animal model of atherosclerosis confirmed that PSGL-1 was a major determinant for monocyte recruitment to sites of atherosclerosis (An et al).

Interactions between PSGL-1 and their counter-receptors allow leukocytes to bind weakly and roll on the surface of the vessel where they can sample the endothelial cell-surface micro-environment. Sequestered on the surface of endothelial cells, mainly through charge mediated interactions with cell surface proteoglycans, are small chemotactic cytokines called chemokines. Chemokines bind to (chemokine) receptors on the surface of the leukocyte to up-regulate expression of adhesion molecules on the surface of the mononuclear cells and to promote cyto-skeletal rearrangement.

The most important chemokine/receptor interaction for the firm adhesion of monocytes to endothelial cells is between MCP-1/CCL2 and CCR2 (see, for review, Barlic and Murphy, *J. Leukoc. Biol.* 82, 2007, 226-236). The level of expression of CCR2 on the surface of monocytes is an important determinant of the potential for monocyte recruitment (Weber C 1999). The direct effect of MCP-1/CCL2 on the adhesion of monocytes to endothelial cells is through up-regulation of integrin expression on the monocyte cell surface; these adhesion molecules bind to their counter-receptors, members of the super-immunoglobulin family, expressed on the surface of endothelial cells.

MCP-1/CCL2 ligation of CCR2 can rapidly promote conformational change in cell surface expressed Mac-1 (CD11b/CD18) a leukocyte $\beta_2$-integrin; there is significant direct and circumstantial evidence for this integrin in the pathogenesis of CKD. There is both up-regulation of expression and a rapid change in conformation of the molecule to a high avidity state. These processes promote monocyte recruitment.

A further important pathway for the recruitment of monocytes in atherogenesis is through the chemokine fractalkine/CX3CL1, which is expressed by endothelial cells and it's ligand, CX3CR1, expressed on mononuclear cells including monocytes. CX3CL1 is an atypical, multimodular chemokine, which exists in membrane-tethered and soluble forms. The immobilized form consists of a chemokine domain anchored to the plasma membrane through an extended, mucin-like stalk, a transmembrane helix, and an intracellular domain. Full-length transmembrane CX3CL1 functions as an intercellular adhesion molecule, which mediates integrin-independent cell capture by binding to CX3CR1 on target cells. In atherosclerosis, both molecules are expressed on foam cells and coronary artery SMCs in both species, where the adhesion chemokine receptor CX3CR1 and its ligand CX3CL1 are up-regulated, promoting monocyte/macrophage capture and retention in the plaque (see, for review, Barlic and Murphy, *J. Leukoc. Biol.* 82, 2007, 226-236).

Recently it has been clearly shown that the relative contributions of CCR2 and CX3CR1 to leukocyte recruitment are similar, and knocking out both pathways has an additive effect on down-regulating mononuclear recruitment and the progression of atherosclerosis.

On recruitment to the arterial intima, the macrophage serves many functions related to atherosclerosis and its complications. Notably, it can secrete pro-inflammatory cytokines that amplify the local inflammatory response in the lesion, as well as reactive oxygen species. The activated mononuclear phagocyte plays a key role in the thrombotic complications of atherosclerosis by producing matrix metalloproteinases (MMPs) that can degrade extracellular matrix that lends strength to the plaque's fibrous cap.

When the plaque ruptures as a consequence, it permits the blood to contact another macrophage product, the potent pro-coagulant protein tissue factor. Eventually the macrophages congregate in a central core in the typical atherosclerotic plaque. Macrophages can die in this location, some by apoptosis, hence producing the so-called "necrotic core" of the atherosclerotic lesion.

The exact mechanisms relating CVD to the specific conditions of CHD patients are not completely elucidated, and thus potential therapeutic targets may remain. This is of great relevance in end-stage renal failure where a number of molecules of small and middle molecular weight may have a potential pathogenic role. Some of these molecules may activate monocytes, and are not removed by the current generation of dialysers that are in widespread routine use in clinical practice.

Conventionally, CHD patients are treated with high-flux dialyser membranes with a molecular weight cut-off of 15 to 20 kDa in the presence of whole blood. However, when used in convective therapies, namely hemofiltration and hemodiafiltration, proteins with higher mass may pass the high-flux dialyser membrane to some extent.

In order to improve efficiency, a new class of membranes that leak proteins below defined molecular weight cut offs (further referred to as "protein-leaking" membranes) have been developed for hemodialysis more recently. These membranes provide greater clearances of low molecular weight proteins and small protein-bound solutes than conventional high-flux dialysis membranes but at the cost of some albumin loss into the dialysate. While in a small number of clinical trials some improvements could be achieved using protein-leaking membranes, it remains unclear yet that routine use of protein-leaking membranes is warranted. It is also unclear whether protein-leaking membranes offer benefits beyond those obtained with conventional high-flux membranes, when the latter are used in convective therapies, such as hemofiltration and hemodiafiltration. Finally, the amount of albumin loss that can be tolerated by hemodialysis patients in a long-term therapy has yet to be determined (Ward, R. A., *J. Am. Soc. Nephrol.* 16, 2005, 2421-2430).

WO 2004/056460 discloses high cut-off (HCO) membranes which can be used in dialysers to eliminate circulating sepsis-associated inflammatory mediators more effectively than using conventional dialysis membranes. These high cut-off membranes, have much higher pore size than the above mentioned types. Pore sizes are in the range of 20 to 40 nm, three times larger than conventional (slightly) protein-leaking membranes and by a factor of four larger than the standard high flux membranes (12 nm and 9 nm, respectively). The high cut-off membranes have a molecular weight cut-off, measured in the presence of whole blood, of 45 kDa whereas the cut-off of the other types of membranes usually does not exceed 20 kDa (see also above). This cut-off measured in blood clearly indicates that substances, like smaller proteins, with a molecular weight from 20 to 45 kDa can penetrate these high cut-off membranes to a significant degree.

Recently, a remarkable clearance of interleukin-6 (IL-6) with high cut-off treatments leading to a significant decrease in circulating IL-6 levels in septic patients suffering from acute renal failure was demonstrated (Morgera, S., et al., *Intensive Care Med.* 29, 2003, 1989-1995). Furthermore, such treatment led to a restoration of immunoresponsiveness of blood cells in those patients (Morgera S., et al., *Nephrol. Dial. Transplant.* 18, 2003, 2570-2576). A study where patients were randomly allocated to high cut-off, continuous veno-venous hemofiltration (CVVH) or hemodialysis (CVVHD) showed that convection and diffusion did not exhibit the expected difference in terms of clearance of middle-molecular-weight proteins, whereas using diffusion instead of convection significantly reduces the loss of albumin while maintaining good cytokine clearance rates. In CVVHD mode, a maximum albumin loss of 950 mg per hour in patients treated with the HCO membrane was reported (Morgera S., et al., *Am. J. Kidney Dis.* 43, 2004, 444-453).

EP 1 852 136 A1 discloses a method of reducing blood free light chain concentration in a subject suffering from multiple myeloma, wherein the subject's blood is subjected to hemodialysis, hemodiafiltration or hemofiltration by using a HCO dialysis membrane to reduce blood free light chain concentration in the patient. In this way, chronic renal failure is prevented or slowed.

The applicants have now found that such membranes can also be used to effectively treat end stage renal failure (ESRD) patients.

SUMMARY OF THE INVENTION

According to one aspect of the invention, a dialysis membrane that allows the passage of molecules having a molecular weight of up to 45 kDa in the presence of whole blood, and with a molecular weight exclusion limit in water of about 200 kDa is provided for the treatment of an ESRD patient. The present invention also provides a dialysis membrane for reducing the risk of cardiovascular disease in ESRD patients. This is through providing a dialysis membrane for the reduction of monocyte activation in the blood of an ESRD patient, as indicated by the down-regulation of monocyte cell surface proteins, especially of PSGL-1 (CD162), Mac-1 (CD11b/18), CCR2 and CX3CR1. Another aspect of the present invention is a hemodialysis device for conducting hemodialysis on an ESRD patient, comprising a dialysis membrane that allows the passage of molecules having a molecular weight of up to 45 kDa in presence of whole blood, and with a molecular weight exclusion limit in water of about 200 kDa.

The dialysis membrane is most advantageously used for the treatment of an ESRD patient. In terms of the international CKD classification, ESRD patients are those patients with stage 5 chronic kidney failure requiring long term renal replacement therapy, which may include hemodialysis.

DETAILED DESCRIPTION

Figure 1:
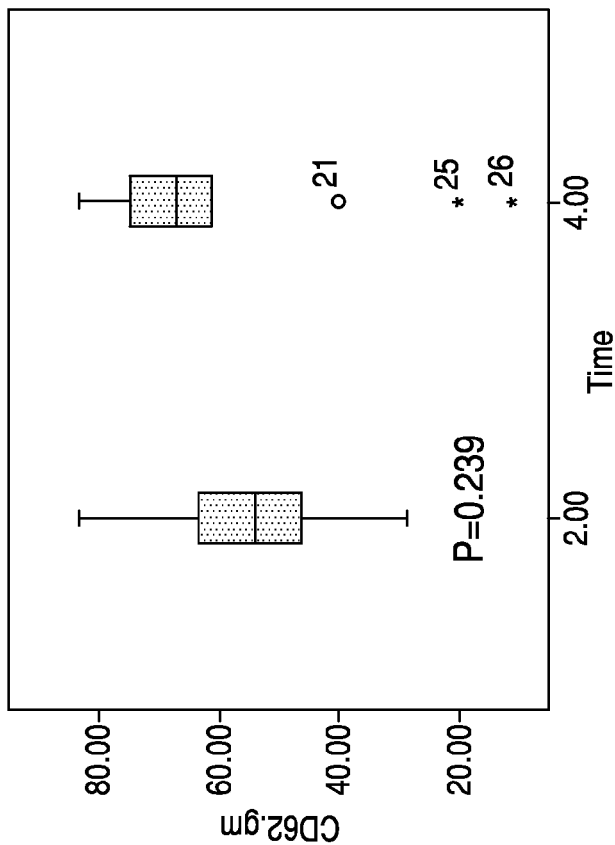
FIG. 1 shows the percentage of L-selectin (CD62L) before and after two weeks HCO-HD. No change in % of CD62L +ve cells is observed. No significant change in mean fluorescence is observed.
Figure 1:
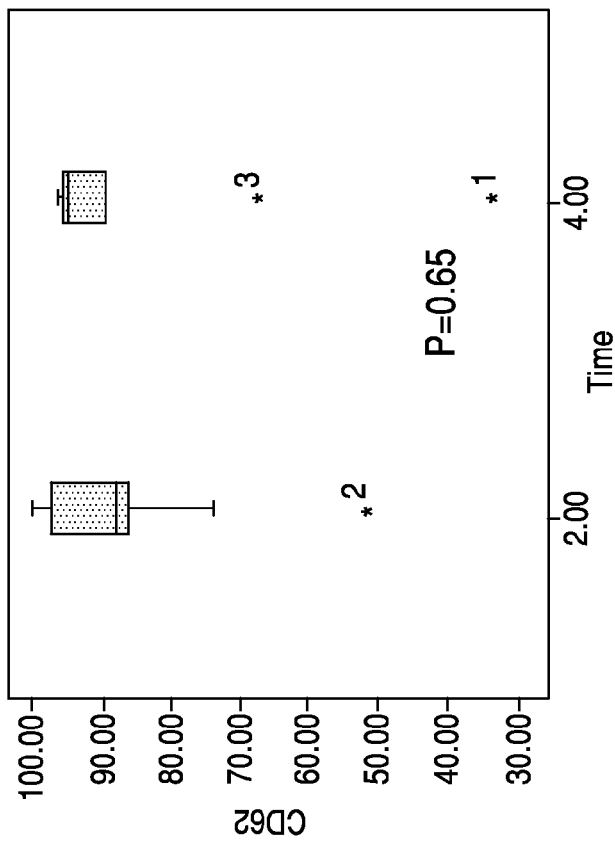
Figure 2:
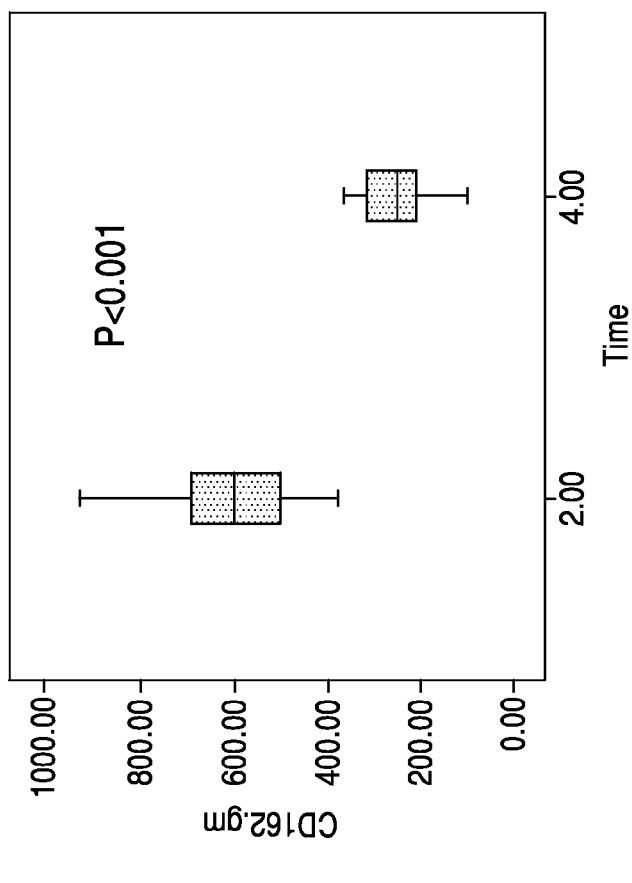
FIG. 2 shows the percentage of Selectin-P ligand (CD162) before and after two weeks HCO-HD. No change in % of CD62L +ve cells is observed. Mean fluorescence decreased.
Figure 2:
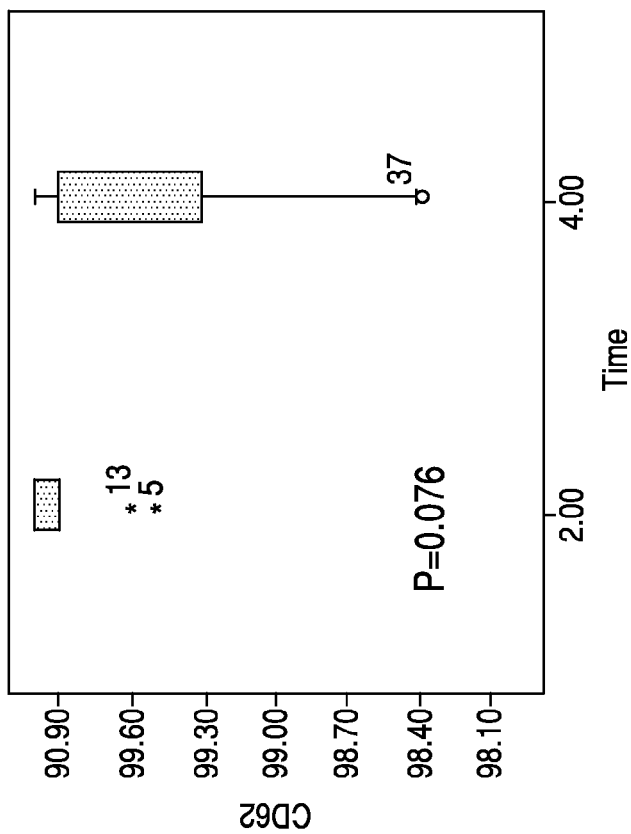
Figure 3:
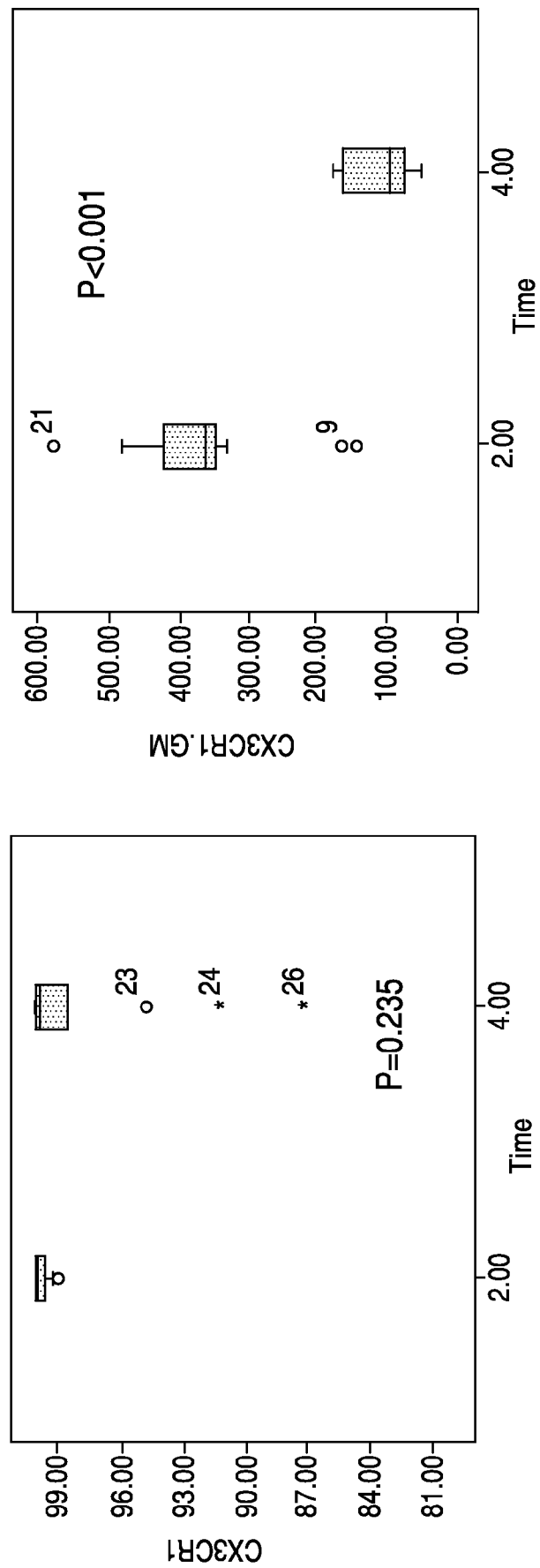
FIG. 3 shows the percentage of CX3CR1 before and after two weeks HCO-HD. No change in % of CX3CR1 +ve cells is observed. Mean fluorescence decreased.
Figure 4:
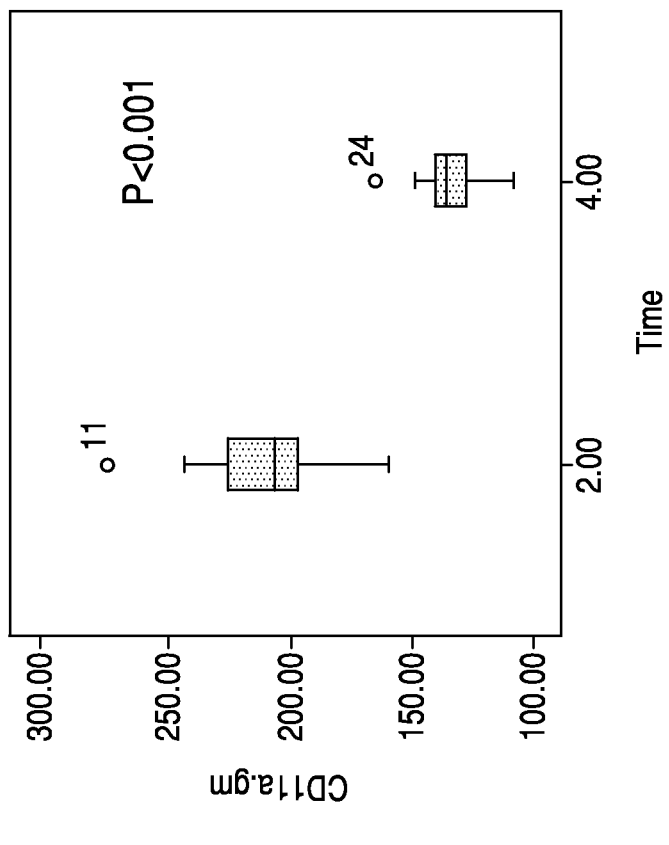
FIG. 4 shows the percentage of CD11a before and after two weeks HCO-HD. A reduction in % of CD11a +ve cells is observed. Mean fluorescence decreased.
Figure 4:
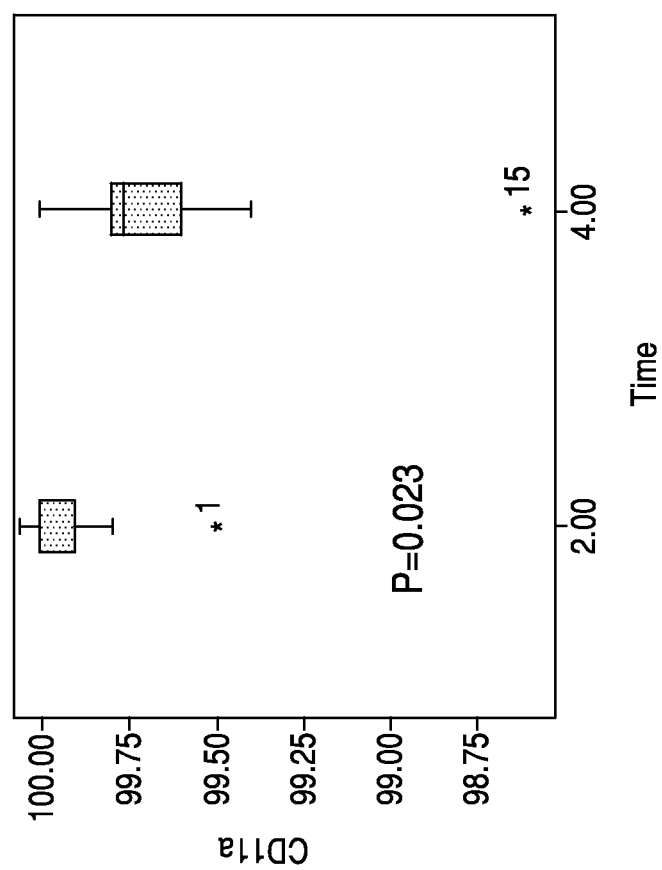
Figure 5:
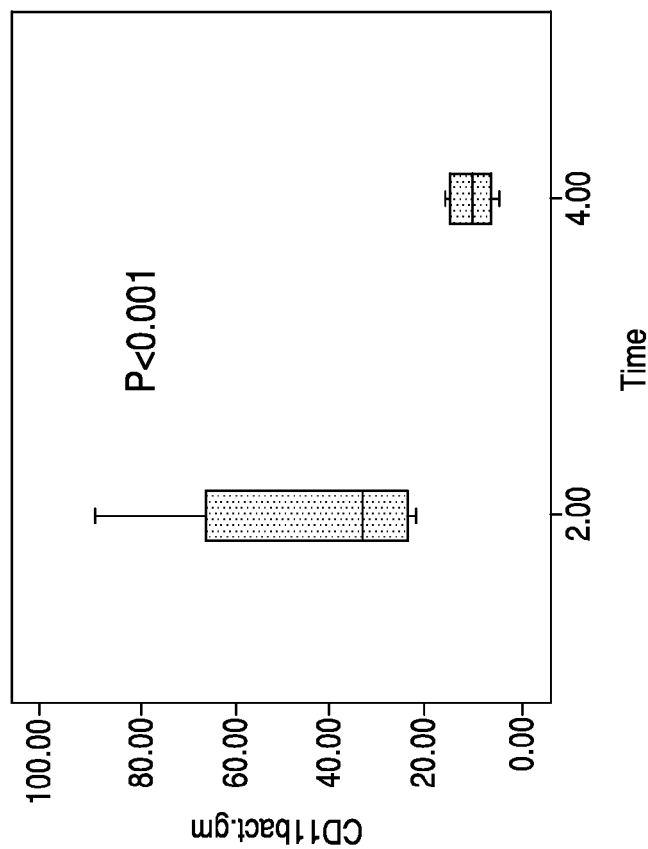
FIG. 5 shows the percentage of MAC-1 (Integrin-α/CD11b) active before and after two weeks HCO-HD. A reduction in % of CD11b active +ve cells is observed. Mean fluorescence decreased.
Figure 5:
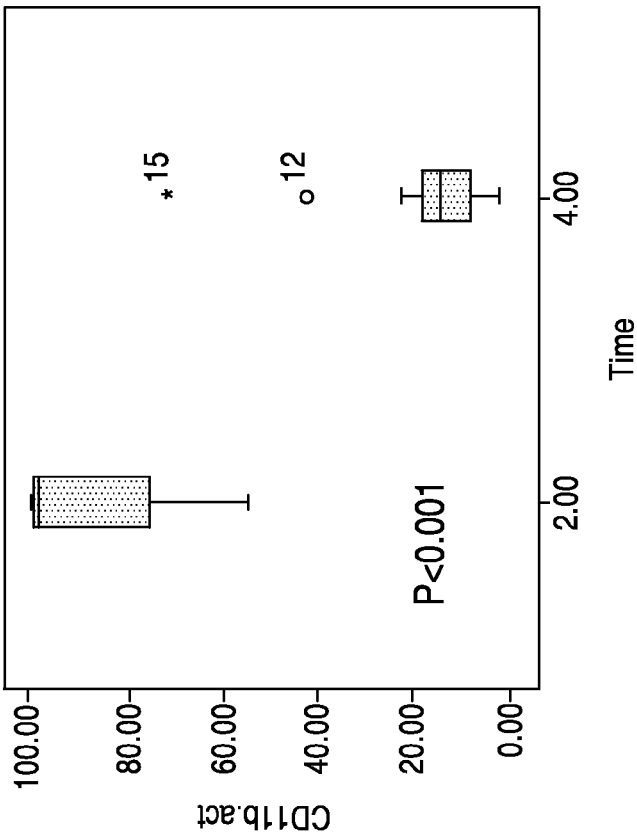
Figure 6:
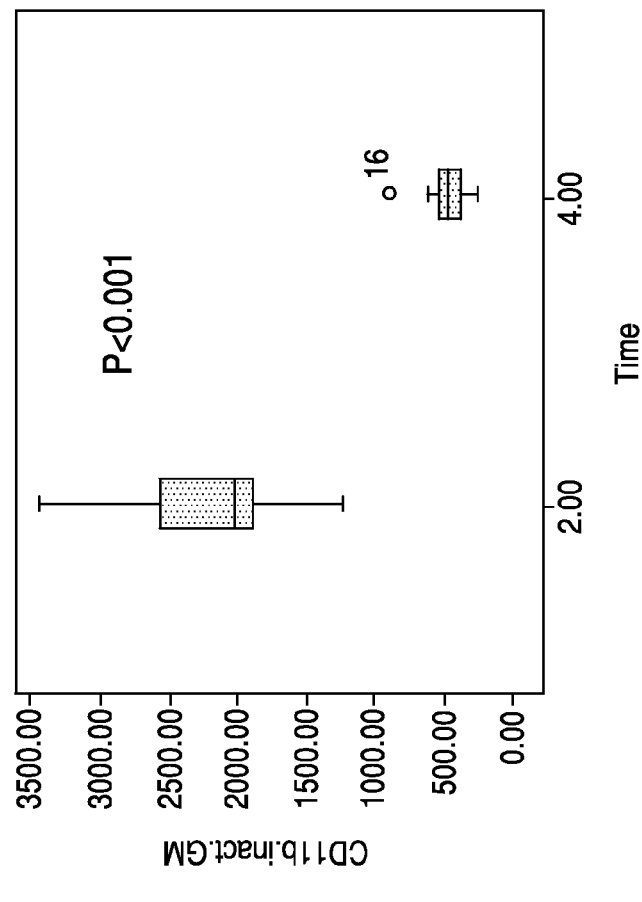
FIG. 6 shows the percentage of MAC-1 (CD11b) inactive before and after two weeks HCO-HD. A reduction in % of CD11b inactive +ve cells is observed. Mean fluorescence decreased.
Figure 6:
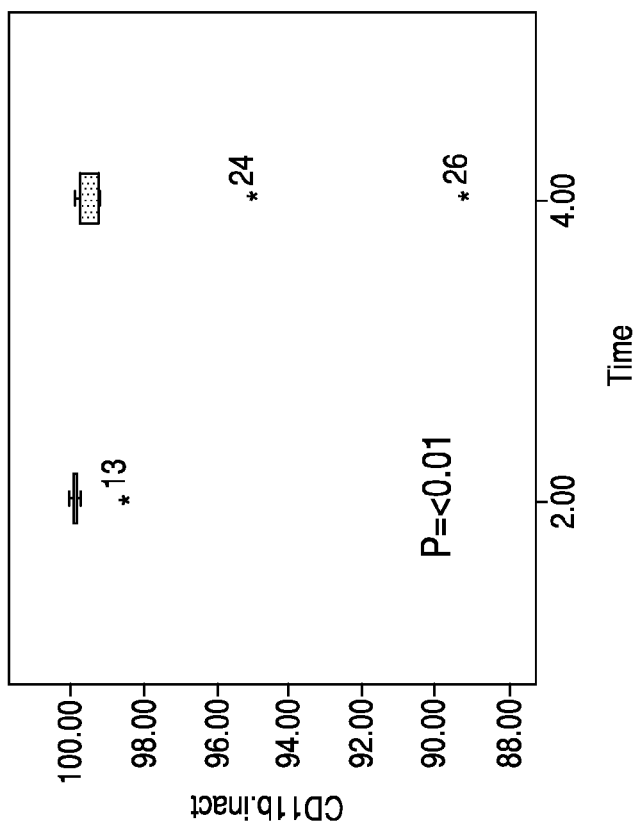
Figure 7:
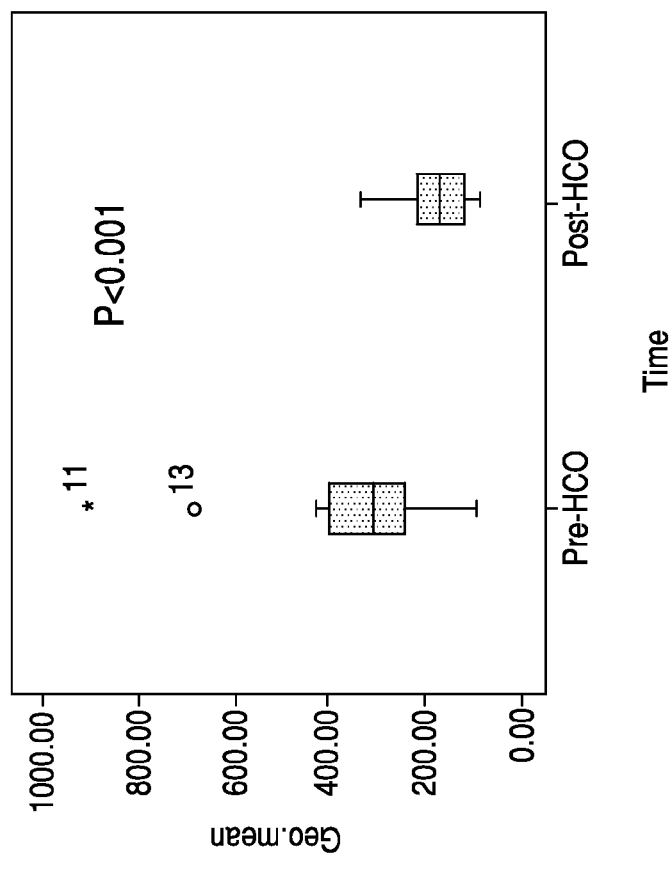
FIG. 7 shows the percentage of CCR2 before and after two weeks HCO-HD. No change in % of CCR2 +ve cells is observed. Mean fluorescence decreased.
Figure 7:
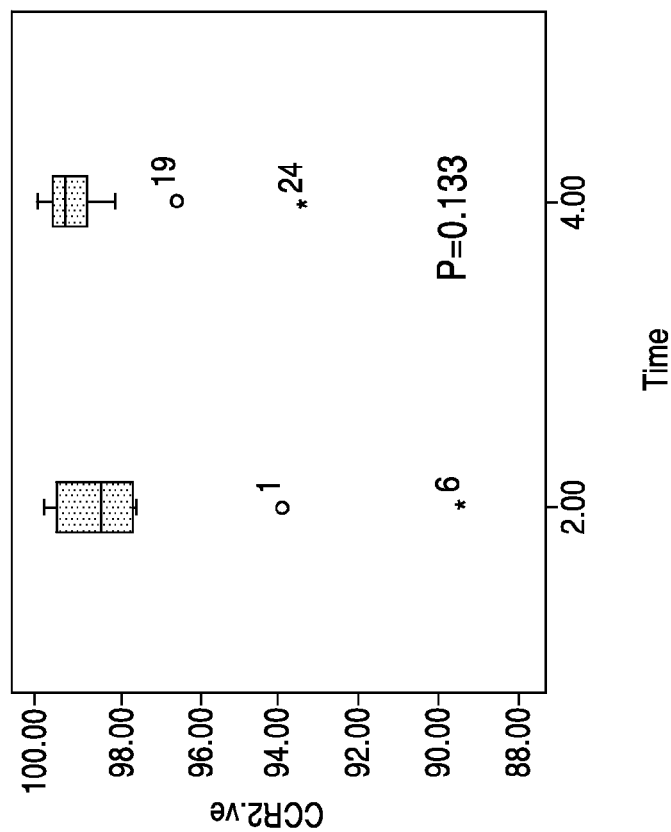
Figure 8:
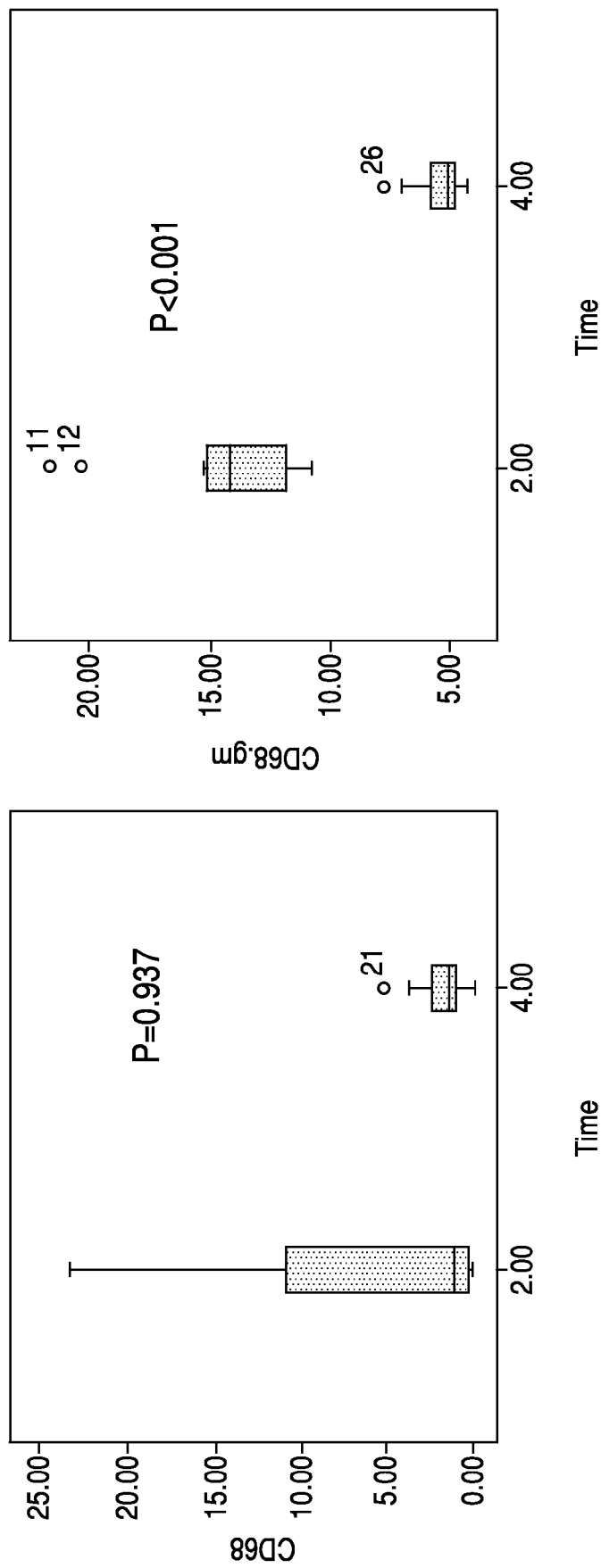
FIG. 8 shows the percentage of CD68 active before and after two weeks HCO-HD. No change in % of CD68 +ve cells is observed. Mean fluorescence decreased.
Figure 9:
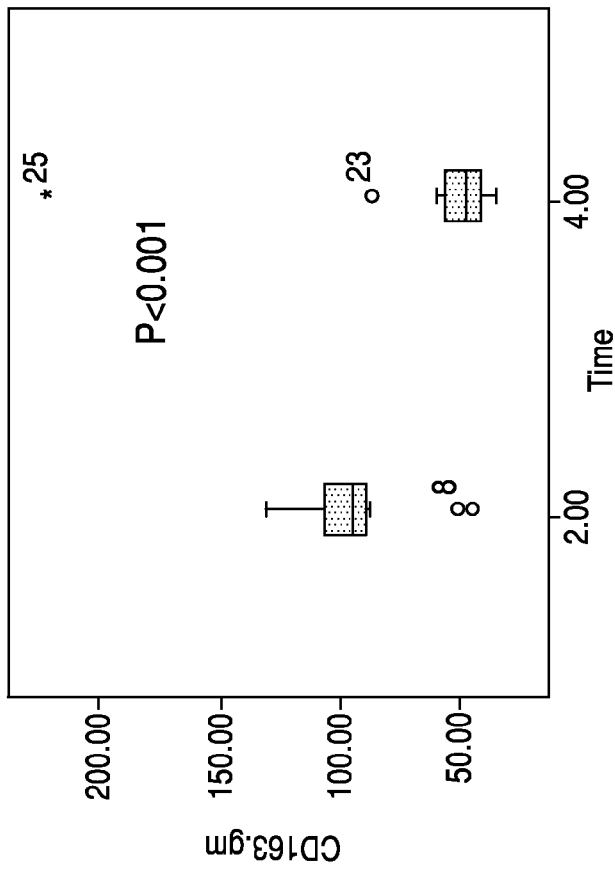
FIG. 9 shows the percentage of CD163 before and after two weeks HCO-HD. No change in % of CD163 +ve cells is observed. Mean fluorescence decreased.
Figure 9:
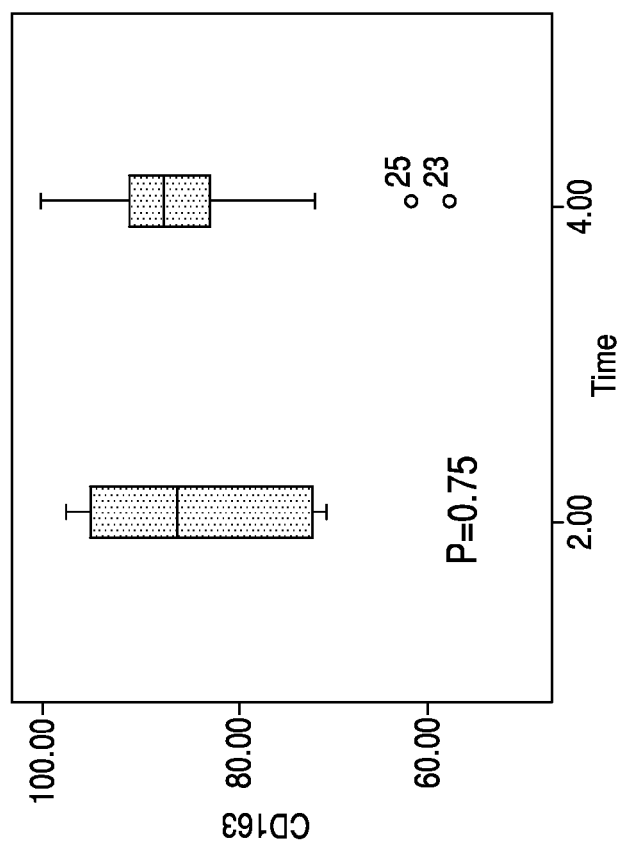
Figure 10:
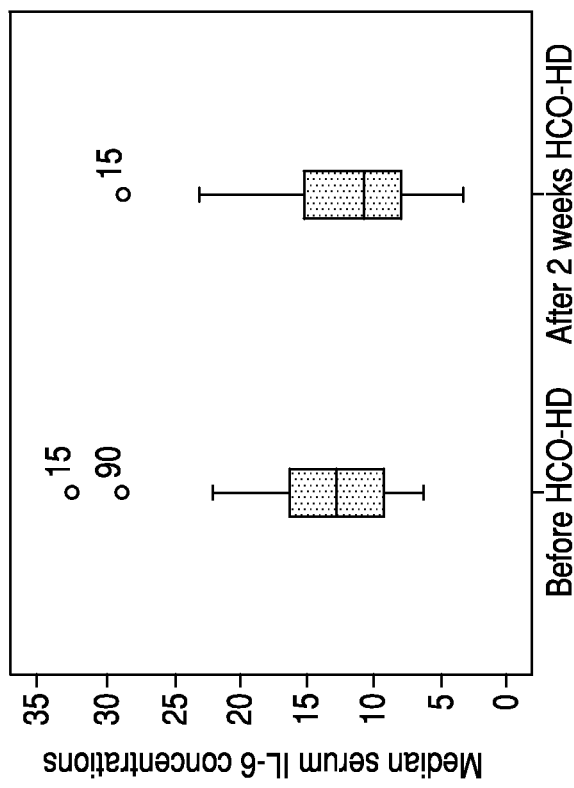
FIG. 10 shows the change of serum concentration of IL-6 (21 kDa) during one session of high flux HD or HCO-HD, respectively (left), and pre-dialysis serum concentrations of IL-6 before and after two weeks HCO-HD (right).
Figure 10:
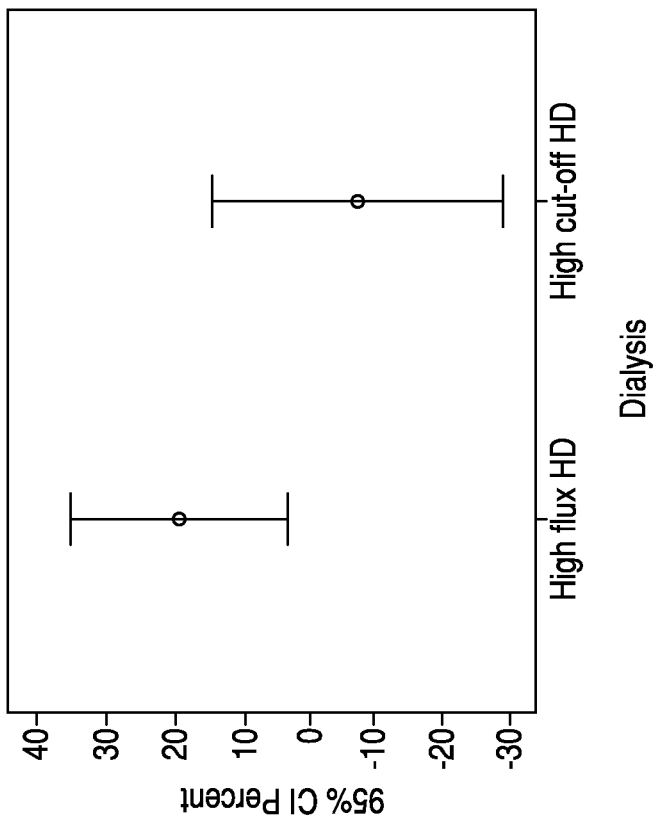
Figure 11:
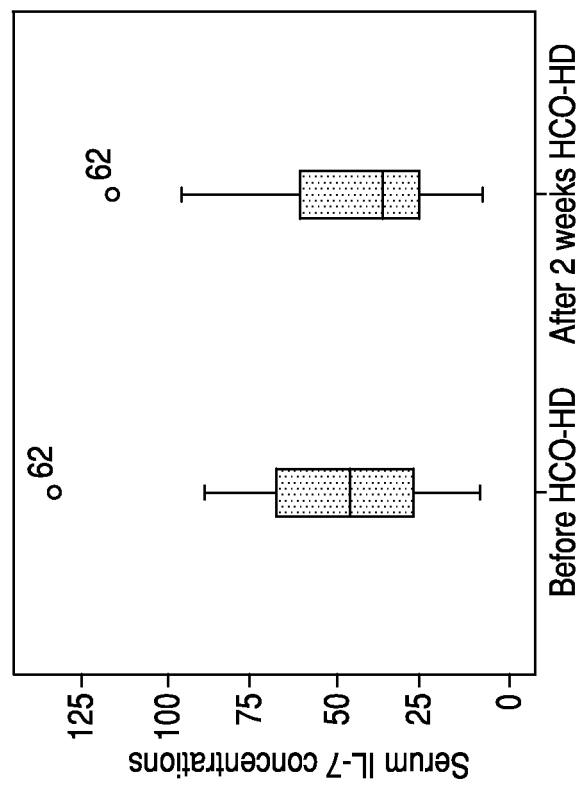
FIG. 11 shows the change of serum concentration of IL-7 (20-28 kDa) during one session of high flux HD or HCO-HD, respectively (left), and pre-dialysis serum concentrations of IL-7 before and after two weeks HCO-HD (right).
Figure 11:
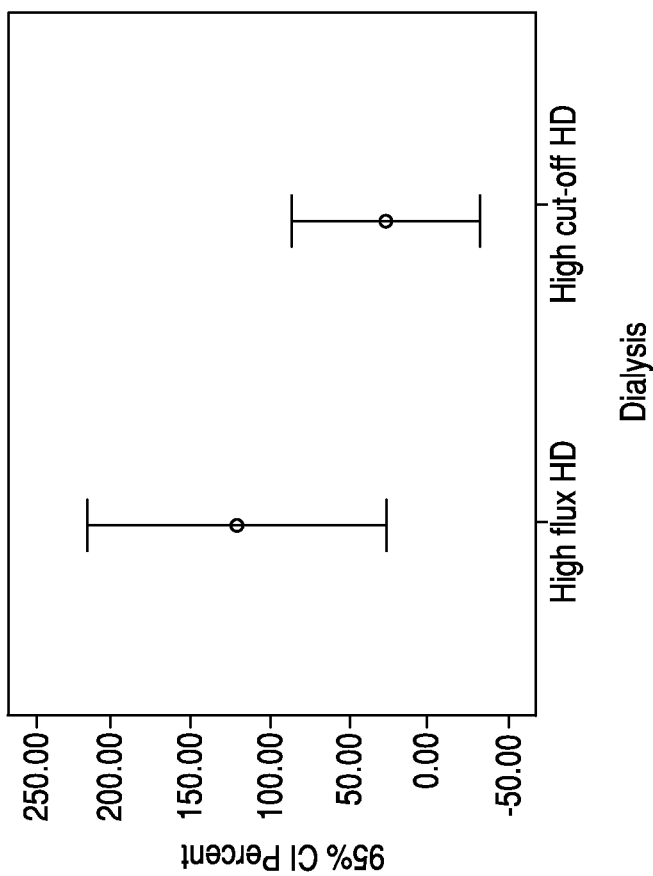
Figure 12:
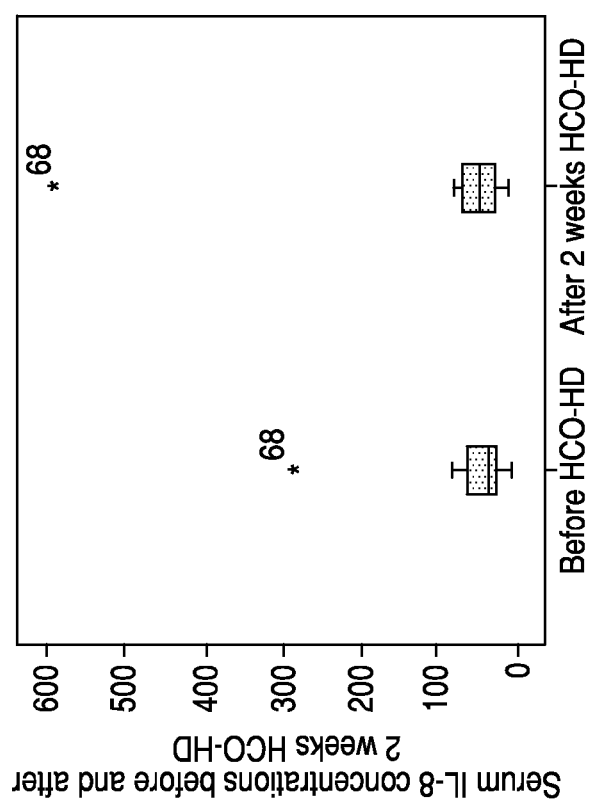
FIG. 12 shows the change of serum concentration of IL-8 (8 kDa) during one session of high flux HD or HCO-HD, respectively (left), and pre-dialysis serum concentrations of IL-8 before and after two weeks HCO-HD (right).
Figure 12:
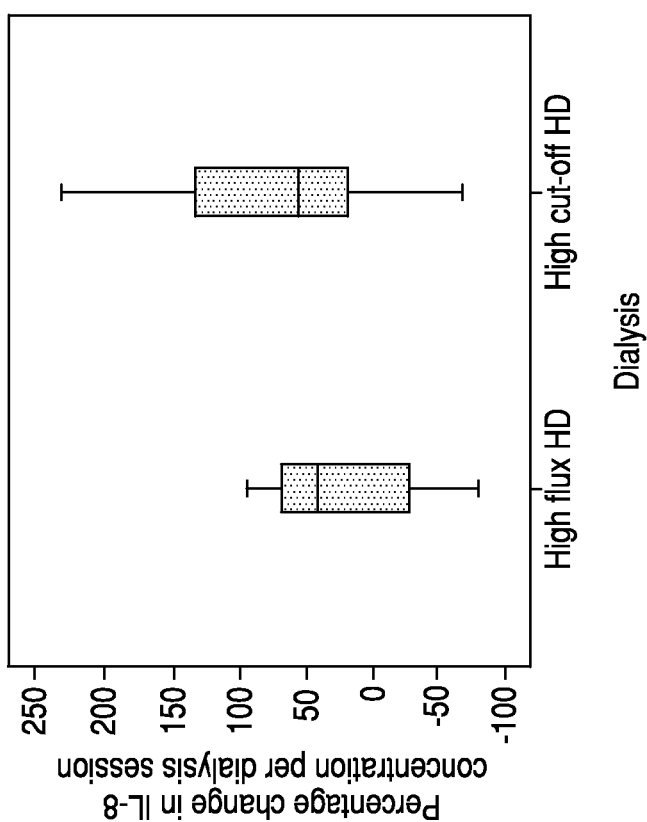
Figure 13:
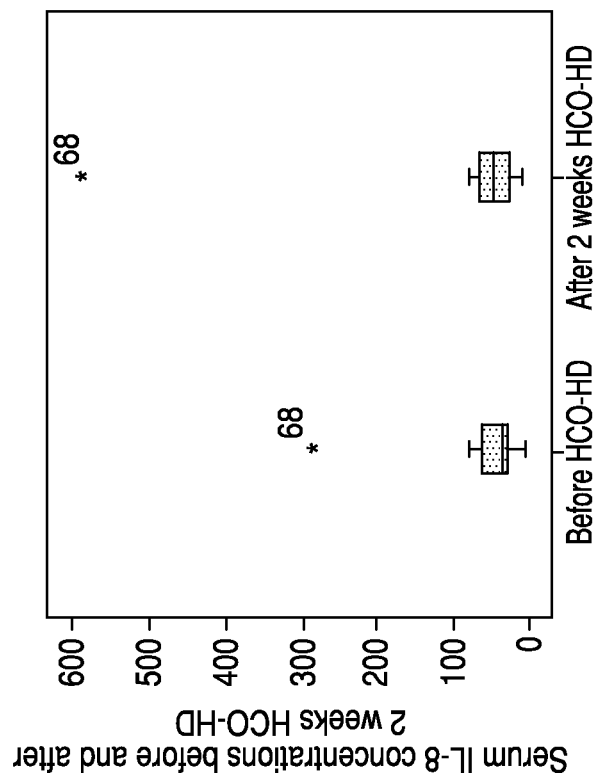
FIG. 13 shows the change of serum concentration of TNFa (25 kDa) during one session of high flux HD or HCO-HD, respectively (left), and pre-dialysis serum concentrations of TNFa before and after two weeks HCO-HD (right).
Figure 13:
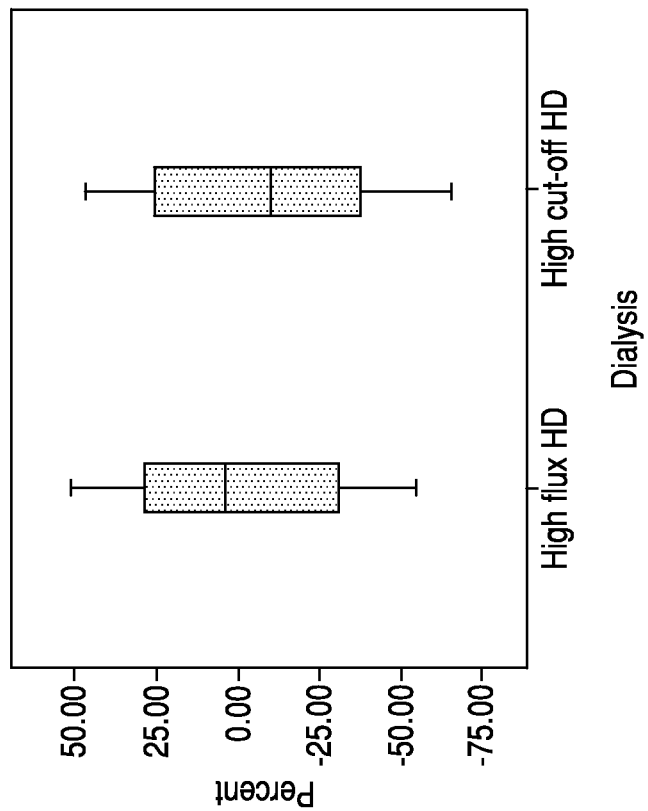

Hemodialysis, hemodiafiltration or hemofiltration according to the invention is preferably carried out using a high cut-off dialysis membrane which has a molecular weight cut-off greater than about 45 kDa, measured in whole blood. Typically, high cut-off membranes have a water permeability of >40 ml/h per mmHg/m$^2$ in vitro. They may have a $\beta_2$-microglobulin clearance of at least 80 ml/min for conventional hemodialysis with a blood flow rate of 300 to 400 ml/min. Albumin loss is preferably 0.5 to 2 g, in particular 1.0 to 1.5 g per hour of dialysis. The sieving coefficient may be 0.9 to 1.0 for $\beta_2$-microglobulin and 0.01 to 0.1, preferably 0.03 to 0.07, for albumin, when measured according to EN 1283. Measured in the presence of whole blood, the sieving coefficient is preferably smaller than 0.05, in particular smaller than 0.01.

More preferably, the membrane is a permselective membrane of the type disclosed in WO 2004/056460. Such membranes preferably allow passage of molecules having a molecular weight of up to 45 kDa in the presence of whole blood and have a molecular weight exclusion limit in water of about 200 kDa. In one embodiment of the invention, the membrane takes the form of a permselective asymmetric hollow fiber membrane. It preferably comprises at least one hydrophobic polymer and at least one hydrophilic polymer. Preferably the polymers are present as domains on the surface.

In one embodiment, the membrane is free light chain (FLC) leaking. That is, the κ or λ free light chains pass through the membrane. High flux membranes, with smaller pore sizes, have been observed to remove some free light chains. However, this appears to be primarily due to binding of the FLC onto the dialysis membranes. FLC may be used as markers of middle molecular weight proteins. Although clearing of free light chains is not a primary target of the invention, their reduction can be used as an indicator of membrane functionality.

According to one aspect of the invention, a dialysis membrane that allows the passage of molecules having a molecular weight of up to 45 kDa in the presence of whole blood, and with a molecular weight exclusion limit in water of about 200 kDa is provided for reducing the risk of cardiovascular disease or retard the progression of cardiovascular disease in a ESRD patient.

Preferably, the cardiovascular disease risk is reduced or the development or progression of cardiovascular disease is slowed irrespective of the patient's inflammatory status.

According to a further aspect of the invention, a dialysis membrane that allows the passage of molecules having a molecular weight of up to 45 kDa in presence of whole blood, and with a molecular weight exclusion limit in water of about 200 kDa is provided for the reduction of monocyte activation in the blood of an ESRD patient. Preferably, monocyte activation can be reduced by the membrane irrespective of the reduction of inflammatory cytokines as set forth below.

The reduction of monocyte activation is indicated by the down-regulation of the expression of cell surface proteins, CD162, CCR2, CX3CR1, and CD11b/18. Methods for the determination of these cell surface proteins are known and include flow cytometry as also set forth below. Advantageously, down-regulation of monocyte cell surface protein expression can further be used to assess CVD risk in the patients.

The treatment is undertaken using a standard hemodialysis machine, provided a endotoxin filter is fitted. Preparation of the membrane is standard to that of any dry membrane i.e. the circuit should be primed with normal saline. The hemodialysis session is normally undertaken for four hours with blood and dialysis flow rates, and ultrafiltration volumes determined on clinical grounds by the supervising physician.

When ESRD patients are treated with hemodialysis using high cut-off membranes ("HCO-HD"), a down-regulation of the expression of particular monocyte surface proteins is observed after several treatment sessions, indicative of a reduction of monocyte activation. In addition, with each dialysis session there was a significantly smaller increase in the concentrations of circulating cytokines (in particular pro-inflammatory) compared with conventional dialysis sessions. Apparently, reduction of monocyte activation also results in reduced formation of circulating cytokines in-between dialysis sessions. Following two weeks treatment with the HCO-HD, there were significant reductions in pre-dialysis concentrations of these cytokines.

According to a further aspect of the invention, a hemodialysis device for conducting hemodialysis on an ESRD patient, especially to reduce the risk of cardiovascular disease, preferably by reducing monocyte activation, is provided, which device comprises a dialysis membrane that allows the passage of molecules having a molecular weight of up to 45 kDa in presence of whole blood, and with a molecular weight exclusion limit in water of about 200 kDa.

Preferably, a dialysis membrane of the invention comprises at least one hydrophilic polymer and at least one hydrophobic polymer. In one embodiment, at least one hydrophilic polymer and at least one hydrophobic polymer are present in the dialysis membrane as domains on the surface of the dialysis membrane.

The hydrophobic polymer may be chosen from the group consisting of polyarylethersulfone (PAES), polypropylene (PP), polysulfone (PSU), polymethylmethacrylate (PMMA), polycarbonate (PC), polyacrylonitrile (PAN), polyamide (PA), or polytetrafluorethylene (PTFE).

The hydrophilic polymer may be chosen from the group consisting of polyvinylpyrrolidone (PVP), polyethyleneglycol (PEG), polyvinylalcohol (PVA), and copolymer of polypropyleneoxide and polyethyleneoxide (PPO-PEO).

In one embodiment, the dialysis membrane is a hollow fiber having at least a 3-layer asymmetric structure with a separation layer present in the innermost layer of the hollow fiber. Preferably the separation layer has a thickness of lees than 0.5 µm. Preferably, the separation layer contains pore channels having a pore size of 15 to 60 nm, more preferably 20 to 40 nm.

The next layer in the hollow fiber membrane is the second layer, having the form of a sponge structure and serving as a support for said first layer. In a preferred embodiment, the second layer has a thickness of about 1 to 15 µm.

The third layer has the form of a finger structure. Like a framework, it provides mechanical stability on the one hand; on the other hand a very low resistance to the transport of molecules through the membrane, due to the high volume of voids. During the transport process, the voids are filled with water and the water gives a lower resistance against diffusion and convection than a matrix with a sponge-filled structure having a lower void volume. Accordingly, the third layer provides mechanical stability to the membrane and, in a preferred embodiment, has a thickness of 20 to 60 µm.

In one embodiment, the membrane also includes a fourth layer, which is the outer surface of the hollow fiber membrane. In this preferred embodiment, the outer surface has openings of pores in the range of 0.5 to 3 µm and the number of said pores is in the range of from 10,000 to 150,000 pores/mm$^2$, preferably 20,000 to 100,000 pores/mm$^2$. This fourth layer preferably has a thickness of 1 to 10 µm.

The manufacturing of the membrane of the present invention follows a phase inversion process, wherein a polymer or a mixture of polymers is dissolved in a solvent to form a polymer solution. The solution is degassed and filtered and is thereafter kept at an elevated temperature.

Subsequently, the polymer solution is extruded through a spinning nozzle (for hollow fibers) or a slit nozzle (for a flat film) into a fluid bath containing a non-solvent for the polymer. The non-solvent replaces the solvent and thus the polymer is precipitated to an inverted solid phase.

To prepare a hollow fiber membrane, the polymer solution preferably is extruded through an outer ring slit of a nozzle having two concentric openings. Simultaneously, a center fluid is extruded through an inner opening of the nozzle. At the outlet of the spinning nozzle, the center fluid comes in contact with the polymer solution and at this time the precipitation is initialized. The precipitation process is an exchange of the solvent from the polymer solution with the non-solvent of the center fluid.

Through this exchange, the polymer solution inverses its phase from the fluid into a solid phase. In the solid phase the pore structure, i.e. asymmetry and the pore size distribution, is generated by the kinetics of the solvent/non-solvent exchange. The process works at a certain temperature which influences the viscosity of the polymer solution. The temperature at the spinning nozzle and the temperature of the polymer solution and center fluid is 30 to 80° C. The viscosity determines the kinetics of the pore-forming process through the exchange of solvent with non-solvent. Subsequently, the membrane is preferably washed and dried.

By the selection of precipitation conditions, e.g. temperature and speed, the hydrophobic and hydrophilic polymers are "frozen" in such a way that a certain amount of hydrophilic end groups are located at the surface of the pores and create hydrophilic domains. The hydrophobic polymer builds other domains. A certain amount of hydrophilic domains at the pore surface area are needed to avoid adsorption of proteins. The size of the hydrophilic domains should preferably be within the range of 20 to 50 nm. In order to repel albumin from the membrane surface, the hydrophilic domains also need to be within a certain distance from each other. By the repulsion of albumin from the membrane surface, direct contact of albumin with the hydrophobic polymer, and consequently the absorption of albumin, are avoided.

The polymer solution used for preparing the membrane preferably comprises 10 to 20 wt.-% of hydrophobic polymer and 2 to 11 wt.-% of hydrophilic polymer. The center fluid generally comprises 45 to 60 wt.-% of precipitation medium, chosen from water, glycerol and other alcohols, and 40 to 55 wt.-% of solvent. In other words, the center fluid does not comprise any hydrophilic polymer.

In a preferred embodiment, the polymer solution coming out through the outer slit openings is, on the outside of the precipitating fiber, exposed to a humid steam/air mixture. Preferably, the humid steam/air mixture has a temperature of at least 15° C., more preferably at least 30° C., and not more than 75° C., more preferably not more than 60° C.

Preferably, the relative humidity in the humid steam/air mixture is between 60 and 100%. Furthermore, the humid steam in the outer atmosphere surrounding the polymer solution emerging through the outer slit openings preferably includes a solvent. The solvent content in the humid steam/air mixture is preferably between 0.5 and 5 wt.-%, related to the water content. The effect of the solvent in the temperature-controlled steam atmosphere is to control the speed of precipitation of the fibers. When less solvent is employed, the outer surface will obtain a more dense surface, and when more solvent is used, the outer surface will have a more open structure. By controlling the amount of solvent within the temperature-controlled steam atmosphere surrounding the precipitating membrane, the amount and size of the pores on the outer surface of the membrane are controlled, i.e. the size of the openings of the pores is in the range of from 0.5 to 3 µm and the number of said pores is in the range of from 10,000 to 150,000 pores/mm$^2$, preferably 20,000 to 100,000 pores/mm$^2$. The fourth layer of the membrane is preferably prepared by this method.

Before the extrusion, suitable additives may be added to the polymer solution. The additives are used to form a proper pore structure and optimize the membrane permeability, the hydraulic and diffusive permeability, and the sieving properties. In a preferred embodiment, the polymer solution contains 0.5 to 7.5 wt.-% of a suitable additive, preferably chosen from the group comprising water, glycerol and other alcohols.

The solvent may be chosen from the group comprising n-methylpyrrolidone (NMP), dimethyl acetamide (DMAC), dimethyl sulfoxide (DMSO) dimethyl formamide (DMF), butyrolactone and mixtures of said solvents.

The sieving coefficient of the membrane for IL-6 in the presence of whole blood is preferably 0.9 to 1.0. Preferably, the sieving coefficient for albumin in the presence of whole blood is less than 0.05.

As used herein, the term "sieving coefficient (S)" refers to the physical property of a membrane to exclude or pass molecules of a specific molecular weight. The sieving coefficient can be determined according to standard EN 1283, 1996.

Put simply, the sieving coefficient of a membrane is determined by pumping a protein solution (bovine or human plasma) under defined conditions (QB, TMP and filtration rate) through a membrane bundle and determining the concentration of the protein in the feed, in the retentate and in the filtrate. If the concentration of the protein in the filtrate is zero, a sieving coefficient of 0% is obtained. If the concentration of the protein in the filtrate equals the concentration of the protein in the feed and the retentate, a sieving coefficient of 100% is obtained.

The sieving coefficient, S, is calculated according to $S=(2C_F)/(C_{Bin}+C_{Bout})$, where $C_F$ is the concentration of a solute in the filtrate; $C_{Bin}$ is the concentration of a solute at the blood inlet side of the device under test; and $C_{Bout}$ is the concentration of a solute at the blood outlet side of the device under test.

Furthermore, the sieving coefficient allows to determine the nominal cut-off of a membrane (corresponding to a sieving coefficient of 0.1). As used herein the term "cut-off" refers to the molecular weight of a substance having a sieving coefficient (S) of 0.1.

The membrane of the present invention allows the passage of molecules having molecular weights up to 45 kDa in the presence of whole blood/blood proteins, which means that it has a sieving coefficient (S) of 0.1 to 1.0 in presence of whole blood for substances having a molecular weight of less than 45 kDa.

Methods for producing suitable membranes are disclosed, for example, in WO 2004/056460, incorporated herein by reference. An example of a suitable membrane is available from Gambro under the trade name "HCO 1100".

As used herein, the term "hemodialysis", HD, refers to a process to correct the chemical composition of blood by removing accumulated metabolic products and adding buffer in a process of diffusion through a natural or synthetic semipermeable membrane.

As used herein, the term "hemodiafiltration", HDF, refers to a process to remove accumulated metabolic products from blood by a combination of diffusive and convective transport through a semi-permeable membrane of high-flux type; fluid is removed by ultrafiltration and the volume of filtered fluid exceeding the desired weight loss is replaced by sterile, pyrogen-free infusion solution.

As used herein, the term "hemofiltration", HF, refers to a process of filtering blood by a membrane with separation of plasma water and solutes with the ultrafiltrate, and retaining all proteins larger than effective pore size and blood cells. In hemofiltration, the accumulated metabolic products are removed from the blood by the process of convective transport as a consequence of ultrafiltration through a semi-permeable membrane of the high flux type; the volume of filtered fluid exceeding the desired weight loss is replaced by sterile pyrogen-free infusion solution.

As used herein, the term "ultrafiltrate" refers to the filtered plasma water and solute and molecules (including free light chains) smaller than the effective pore size.

It will be readily apparent to one skilled in the art that various substitutions and modifications may be made to the invention disclosed herein without departing from the scope and spirit of the invention.

The present invention will now be illustrated by way of non-limiting examples of preferred embodiments in order to further facilitate the understanding of the invention.

EXAMPLES

Example 1

Thirteen prevalent ESRD patients were recruited into a crossover study. Inclusion criteria: a functioning fistula and normal albumin levels. Exclusion criteria: dialysis catheter, thrombosed fistula, smoker, immunosuppressants, recent infection.

Following a two week wash-in period using a standardized high flux dialyser (Polyflux® 170H, Gambro), patients received two weeks treatment using a high cut-off hemodialyser (HCO 1100™, Gambro). Patients received three dialysis sessions per week of four hours duration each. Blood flow rate was 250 ml/min and dialysate flow rate was 500 ml/min. Blood samples were taken and analyzed, immediately before and after one high flux dialysis session and one high cut-off dialysis session. In addition, blood samples (pre-dialysis) were taken and analyzed at the start and end of the two week period of high cut-off hemodialysis.

Blood samples were analyzed for pro-inflammatory cytokines and monocyte activation. Pro-inflammatory cytokines were measured using a 25-Plex AB Bead Kit (BioSource™). Monocyte activation status as determined by expression of surface markers associated with cell trafficking and cell activation was assessed by flow cytometry. The results are shown in FIGS. 1-14.

Figure 14:
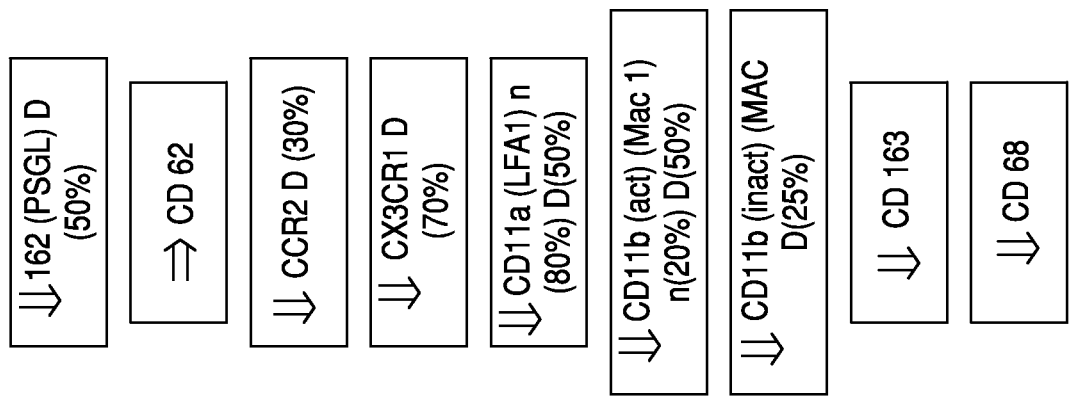
FIG. 14 gives an overview of changes in monocyte cell surface markers.

As can be seen from the figures, after the two weeks HCO-HD treatment, markers of monocyte activation were significantly decreased. Expression of cell surface proteins involved in key stages of monocyte recruitment were reduced (FIG. 14). Surface expression of P-selectin glycoprotein ligand-1 (CD162), a key mediator of early monocyte/endothelium interaction (rolling) was significantly reduced by 50%. Expression of other cell surface proteins involved in the adhesion and migration of monocytes into the extravascular compartment were also reduced: CCR2 (receptor for MCP-1, involved in monocyte migration) reduced by 30%; CX3CR1 (receptor for fractalkine, resulting in firm adhesion of monocytes) reduced by 70%; CD11a reduced by 80%; CD11b (involved in migration and adhesion of monocytes) reduced by 20%; CD163 reduced by 50% and CD68 was reduced by 50% (all $P<0.01$). In addition, there was a global decrease in pre-dialysis serum concentrations of pro-inflammatory cytokines following two weeks treatment with HCO-HD ($P<0.001$).

Example 2

Fifteen prevalent ESRD patients showing elevated CRP levels were recruited into a crossover study. Following a three week wash-in period using a standardized high flux dialyser (Polyflux® 170H, Gambro), patients received three weeks treatment using a high cut-off hemodialyser (HCO 1100™, Gambro) followed by three weeks treatment using a standardized high flux dialyser (Polyflux®170H, Gambro).

Patients received three dialysis sessions per week of four hours duration each. Blood flow rate was 250 ml/min and dialysate flow rate was 500 ml/min.

Figure 15:
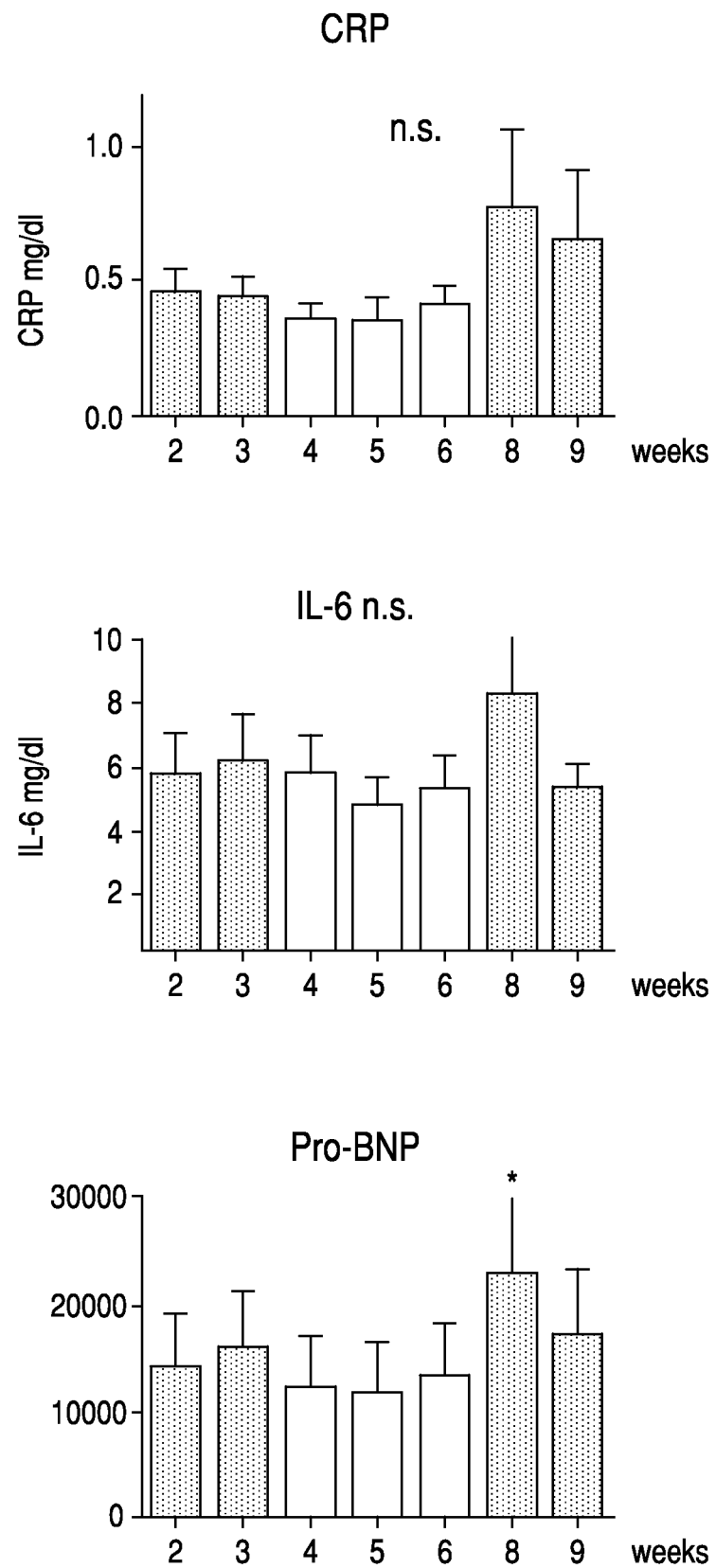
FIG. 15 shows the average concentrations of CRP, IL-6, and pro-BNP in the patients' blood in weeks 2 through 9 of the study.
Figure 16:
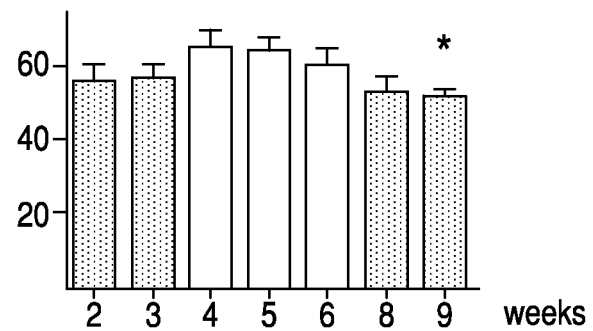
FIG. 16 shows the average number of CD162 granulocytes, CD162 monocytes, and CD162 leukocytes in the patients' blood in weeks 2 through 9 of the study.
Figure 16:
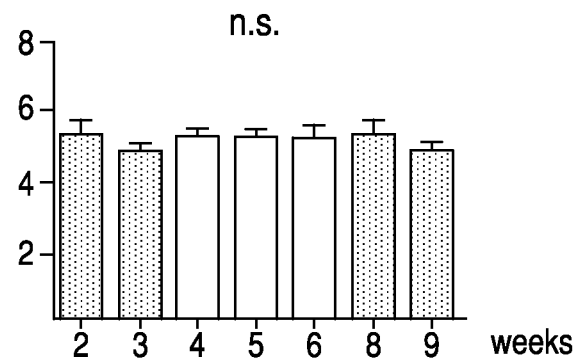
Figure 16:
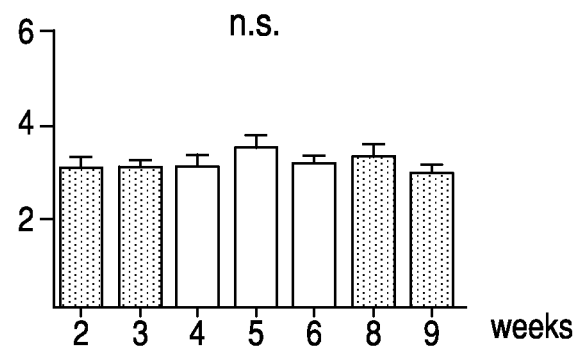
Figure 17:
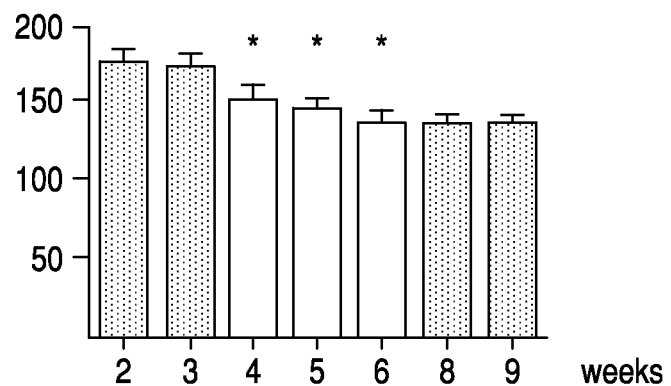
FIG. 17 shows the average number of CD181 granulocytes, CD181 monocytes, and CD181 leukocytes in the patients' blood in weeks 2 through 9 of the study.
Figure 17:
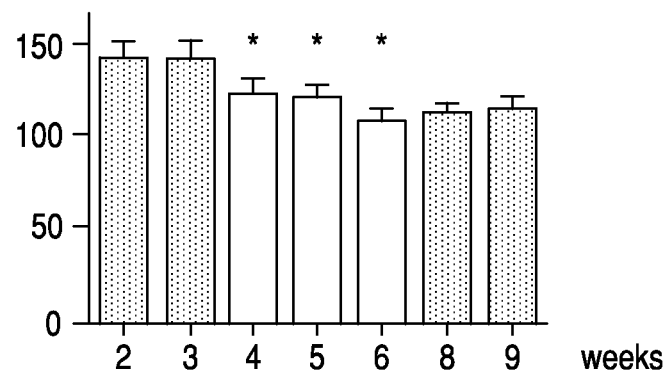
Figure 17:
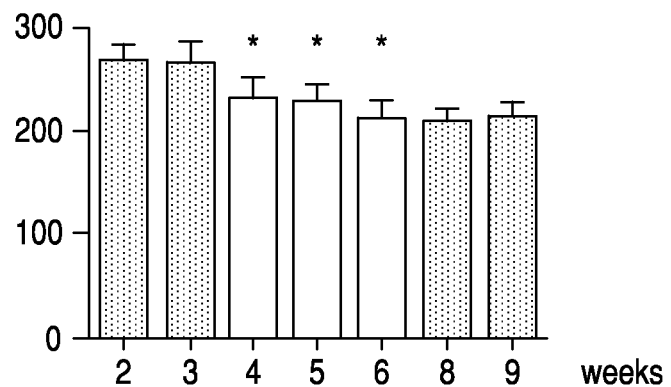

Blood samples were taken weekly and analyzed for content of CRP, IL-6, pro-BNP and other parameters. In addition, pulse wave velocities (PWV) in the arteria carotis of ten patients were measured with SphygmoCor at the start and end of the three week period of high cut-off hemodialysis. The results are shown in FIGS. 15-17.

As can be seen from the figures, the lowest concentrations of CRP, IL-6, and pro-BNP, respectively, were found after the three weeks HCO-HD treatment. The expression of CD162 on leukocytes was significantly reduced during use of HCO filter, while at the same time expression of CD181 (CXCR1 chemokine receptor) on granulocytes increased, both approaching the normal range. PWV (which is an indicator of blood vessel rigidity) decreased with marginal significance during the phase of HCO-HD treatment.

The invention claimed is:

1. A method of treating a subject suffering from end stage renal disease against cardiovascular disease, the method comprising hemodialyzing, hemofiltering or hemodiafiltering the blood of the subject using a dialysis membrane that permits passage of molecules having a molecular weight of up to 45 kD in the presence of whole blood to reduce the activation of monocytes in the blood of the subject.

2. The method of claim 1, wherein the reduction of monocyte activation is indicated by the down-regulation of the expression of monocyte cell surface proteins.

3. The method of claim 2, wherein the monocyte cell surface proteins are selected from the group consisting of PSGL-1 (CD162), CCR2, CX3CR1, and CD11b.

4. The method of claim 1, wherein the reduction of monocyte activation is indicated by the reduction of pre-dialysis concentrations of circulating pro-inflammatory cytokines.

5. The method of claim 1, wherein at least one hydrophilic polymer and at least one hydrophobic polymer are present in the dialysis membrane as domains on the surface of the dialysis membrane.

6. The method of claim 1, wherein the dialysis membrane is a hollow fiber membrane and has at least a 3-layer asymmetric structure with a separation layer present in the innermost layer of the hollow fiber membrane.

7. The method of claim 6, wherein the membrane has pores in the separation layer, said pores having a diameter in the range of 15 to 60 nm.

8. The method of claim 7, wherein the pores have a diameter in the range of 20 to 40 nm.

* * * * *

UNITED STATES PATENT AND TRADEMARK OFFICE
CERTIFICATE OF CORRECTION

| | | |
|---|---|---|
| PATENT NO. | : 8,657,775 B2 | Page 1 of 1 |
| APPLICATION NO. | : 12/585054 | |
| DATED | : February 25, 2014 | |
| INVENTOR(S) | : Hutchinson et al. | |

It is certified that error appears in the above-identified patent and that said Letters Patent is hereby corrected as shown below:

Title Page, Item (73) Assignee should read

-- Gambro Lundia AB, Lund (SE) --

Signed and Sealed this
Eighth Day of April, 2014

Michelle K. Lee
*Deputy Director of the United States Patent and Trademark Office*